United States Patent
Reynolds et al.

(10) Patent No.: US 12,171,749 B2
(45) Date of Patent: *Dec. 24, 2024

(54) THIOUREYLENE LIQUID COMPOSITIONS

(71) Applicant: Norbrook Laboratories Limited, Newry (GB)

(72) Inventors: Louise Reynolds, Bandridge (GB); Manish Umrethia, Ahmedabad (IN)

(73) Assignee: NORBROOK LABORATORIES LIMITED, Newry (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/350,152

(22) Filed: Jul. 11, 2023

(65) Prior Publication Data
US 2023/0404978 A1 Dec. 21, 2023

Related U.S. Application Data

(63) Continuation of application No. 17/391,851, filed on Aug. 2, 2021, now Pat. No. 11,738,005, which is a continuation of application No. 16/857,348, filed on Apr. 24, 2020, now Pat. No. 11,123,327, which is a continuation of application No. 16/032,870, filed on Jul. 11, 2018, now abandoned, which is a continuation of application No. 15/321,874, filed as application No. PCT/GB2015/051824 on Jun. 23, 2015, now Pat. No. 10,045,967.

(30) Foreign Application Priority Data

Jun. 25, 2014 (GB) .................................... 1411310

(51) Int. Cl.
| | | |
|---|---|---|
| A61K 31/4164 | (2006.01) | |
| A61K 9/00 | (2006.01) | |
| A61K 9/08 | (2006.01) | |
| A61K 47/02 | (2006.01) | |
| A61K 47/10 | (2017.01) | |
| A61K 47/12 | (2006.01) | |
| A61K 47/14 | (2017.01) | |
| A61K 47/26 | (2006.01) | |
| A61K 47/32 | (2006.01) | |
| A61K 47/34 | (2017.01) | |
| A61K 47/36 | (2006.01) | |
| A61K 47/44 | (2017.01) | |

(52) U.S. Cl.
CPC ........ *A61K 31/4164* (2013.01); *A61K 9/0053* (2013.01); *A61K 9/0095* (2013.01); *A61K 9/08* (2013.01); *A61K 47/02* (2013.01); *A61K 47/10* (2013.01); *A61K 47/12* (2013.01); *A61K 47/14* (2013.01); *A61K 47/26* (2013.01); *A61K 47/32* (2013.01); *A61K 47/34* (2013.01); *A61K 47/36* (2013.01); *A61K 47/44* (2013.01)

(58) Field of Classification Search
None
See application file for complete search history.

(56) References Cited

U.S. PATENT DOCUMENTS

| | | |
|---|---|---|
| 4,096,174 A | 6/1978 | Conrow et al. |
| 5,310,742 A | 5/1994 | Elias |
| 10,045,967 B2 | 8/2018 | Reynolds et al. |
| 11,123,327 B2 | 9/2021 | Reynolds et al. |
| 11,738,005 B2 | 8/2023 | Reynolds et al. |
| 2005/0158367 A1 | 7/2005 | Hershberger |
| 2018/0318262 A1 | 11/2018 | Reynolds et al. |

FOREIGN PATENT DOCUMENTS

| | | |
|---|---|---|
| DE | 3013839 A1 | 10/1980 |
| GB | 2050828 B | 11/1983 |
| WO | WO-2001083093 A1 | 11/2001 |
| WO | WO-2007087623 A2 | 8/2007 |
| WO | WO-2009062939 A1 | 5/2009 |

OTHER PUBLICATIONS

"2.2.3 Potentiometric Determination of Ph," Europeans Pharmacopeia 8.0, Feb. 2014: pp. 24-25.
Combined Search and Examination Report issued by the United Kingdom for related application No. GB1411310.4, mailed Feb. 19, 2015.
Crowley, "Solutions, Emulsions, Suspensions, and Extracts," Remington: The Science and Practice of Pharmacy 21st ed. (Lippincott Williams & Wilkins, Philadelphia, PA, US, 206) pp. 745-775.
Examination Report issued by the United Kingdom for Related application No. GB1411310.4, mailed Aug. 18, 2016.
Ginsberg "Diagnoisis ad management of Graves' disease" CMAJ, 2003; 168(d): pp. 575-585.
International Search Report and Written Opinion for PCT/GB2015/051824 mailed Aug. 6, 2015.
Mori, Akihori, Internal treatment and nutritional management of thyroid diseases, Pet-Eiyogakkaishi, 2012, vol. 15, II, pp. 111-114.
Office Action issued Jul. 2, 2019, for corresponding JP Appl. No. 2016-575086.
U.S. Department of Health and Human Services, Food and Drug Administration, Center for Drug Evaluation and Research (CDER), "Bioavailability and Bioequivalence Studies for Orally Administered Drug Products—General Considerations," Guidance for Industry (2002).

*Primary Examiner* — Samantha L Shterengarts
(74) *Attorney, Agent, or Firm* — Wilson Sonsini Goodrich & Rosati

(57) ABSTRACT

The present invention relates to novel liquid compositions and formulations containing a thioureylene compound, a polysaccharide and a liquid vehicle. The compositions and formulations of the invention are useful for dealing with diseases and conditions associated with abnormally high thyroid hormone levels in mammals, such as humans and cats.

19 Claims, 1 Drawing Sheet

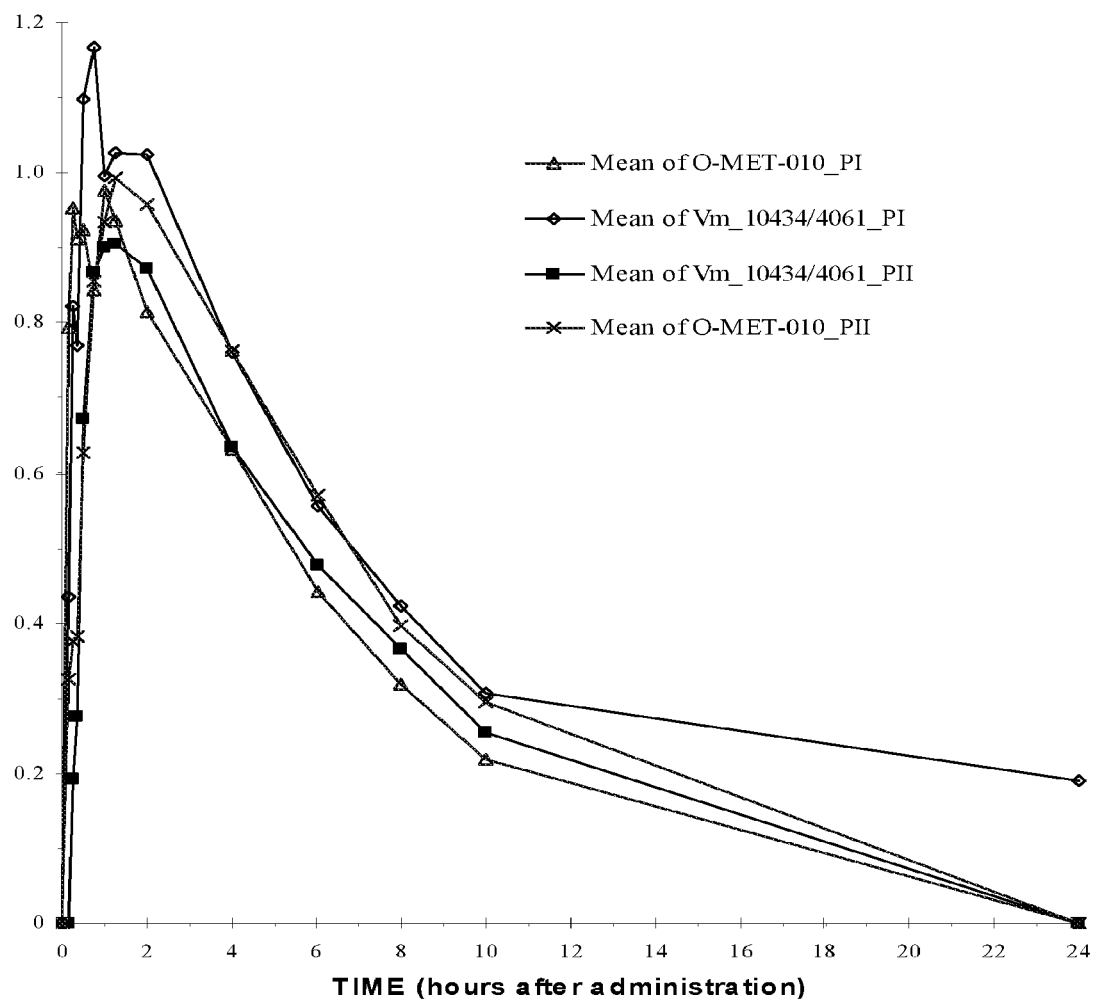

THIOUREYLENE LIQUID COMPOSITIONS

CROSS-REFERENCE TO RELATED APPLICATIONS

This application is a continuation of Ser. No. 17/391,851 filed Aug. 2, 2021, which is a continuation of Ser. No. 16/857,348 filed Apr. 24, 2020 with U.S. Pat. No. 11,123,327, which is a continuation of Ser. No. 16/032,870 filed Jul. 11, 2018 which is a continuation of Ser. No. 15/321,874 filed Dec. 23, 2016 with U.S. Pat. No. 10,045,967 which is a national stage entry of PCT/GB2015/051824 filed Jun. 23, 2015, each of which is entirely incorporated herein by reference.

TECHNICAL FIELD

The present invention relates to novel liquid compositions containing thioureylene compounds, pharmaceutical formulations based on said compositions and their use for lowering thyroid hormone levels in mammals.

BACKGROUND ART

The thyroid hormones thyroxine ($T_4$) and triiodothyronine ($T_3$) play a significant role in the growth, development and differentiation of normal cells. The production of $T_4$ and $T_3$ is controlled by the thyroid-stimulating hormone (TSH), which is secreted by the hypophysis. An excess of circulating free $T_4$ and $T_3$, or both, is associated with the development of hyperthyroidism (e.g. Grave's disease).

Hyperthyroidism is a relatively common endocrine disorder in mammals and, particularly, in humans and cats. Typical hyperthyroidism treatments include chronic administration of an anti-thyroid medication, surgical removal of the thyroid glands or radioactive iodine therapy. These treatments have their limitations and side effects. For instance, anti-thyroid drugs may be difficult to administer orally, especially if they are in solid form. On the other hand, surgery is an expensive option and may be contraindicated in some cases for older subjects that could suffer from other diseases as well. Finally, radioactive iodine therapy may be administered in licensed facilities only and could require patient hospitalization.

Thioureylenes are anti-thyroid compounds used widely in the treatment of hyperthyroidism. This group of drugs includes carbimazole, methimazole, methylthiouracil and propylthiouracil. See Ginsberg J, et al., CMAJ 2003; 4, 168(5):575-585. Thioureylenes act by inhibiting the enzyme thyroperoxidase, which mediates the synthesis of $T_4$ and $T_3$.

At present, only thioureylene solid formulations have been approved for the treatment of hyperthyroidism in mammals. However, there is a need in the art for alternative thioureylene formulations that could improve or facilitate the treatment of this condition in patients.

DESCRIPTION OF THE FIGURES

FIG. 1 shows the mean plasma levels of methimazole in cats in periods I and II following the oral administration of a formulation according to the present invention and the reference product tablets at a dose rate of 5 mg methimazole per subject.

SUMMARY OF THE INVENTION

The present invention relates to novel liquid compositions and formulations comprising a thioureylene compound, a polysaccharide and a liquid vehicle. The compositions and formulations of the invention are useful for managing diseases and conditions associated with abnormally high thyroid hormone levels, such as hyperthyroidism. Even though the compositions and formulations of the invention are in liquid form, they are surprisingly, stable. They also exhibit a pharmacokinetic profile indistinguishable from other solid thioureylene formulations already approved for human and animal health. At present, there are no stable liquid thioureylene formulations authorized for human or animal use.

The liquid nature of the compositions and formulations of the invention confer them a significant advantage, as they are easier to administer than comparable solid forms. This last trait makes the compositions and formulations of the invention particularly useful for treating mammals and, especially, humans and cats.

Therefore, in a first aspect, the present invention is directed to a composition comprising:

i) about 0.25% to about 1% w/v of a thioureylene compound, a pharmaceutically acceptable salt, solvate, prodrug or combination thereof, ii) at least about 0.2% w/v of a polysaccharide, and iii) a liquid vehicle.

Said composition is characterized specifically for being an stable liquid form.

In a second aspect, the present invention relates to processes of making the liquid compositions according to the first aspect of the invention.

In a third aspect, the present invention relates to a pharmaceutical formulation comprising the liquid composition according to the first aspect of the invention and at least one excipient.

In a fourth aspect, the present invention refers to a liquid composition according to the first aspect of the invention or a pharmaceutical formulation according to the third aspect of the invention for its use as a medicament.

In a fifth aspect, the present invention is directed to liquid composition according to the first aspect of the invention or a pharmaceutical formulation according to the third aspect of the invention for its use in the treatment or prevention of a disease or condition due to increased thyroid hormone levels. Alternatively, the present invention relates to the use of a liquid composition according to the first aspect of the invention in the manufacture of a medicament for the treatment or prevention of a disease or condition associated with increased thyroid hormone levels.

In a sixth aspect, the present invention relates to a method for reducing the thyroid hormone levels in a subject, which comprises administering to the subject a therapeutically effective amount of the liquid composition according to the first aspect of the invention or a pharmaceutical formulation according to the third aspect of the invention.

DESCRIPTION OF THE EMBODIMENTS

1. Definitions

The term "carbimazole", as used herein, refers to ethyl 3-methyl-2-sulfanylidene-imidazole-1-carboxylate, CAS [22232-54-8], a compound of molecular formula $C_7H_{10}N_2O_2S$ and structural formula:

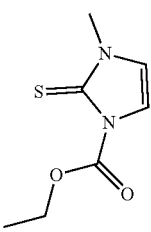

Carbimazole is a methimazole prodrug. After its administration and absorption, carbimazole is converted to methimazole in vivo.

The term "excipient" as used herein, means any component, other than the active substance(s) intentionally added to the formulation of a dosage form. Exemplary excipients are disintegrants, lubricants, plasticizers, binders, fillers, colorants, flavor masking agents, flavoring agents, stabilizers, foaming agents, sweeteners, pore-forming agents, acids (e.g. citric acid, tartaric acid), sodium chloride, a bicarbonate (e.g. sodium, potassium), sugars and alcohols. Some excipients can serve multiple purposes (e.g. filler and disintegrant). See European Pharmacopoeia 8.0.

The term "methimazole", as used herein, refers to 1-methylimidazole-2-thiol, CAS [60-56-0], a compound of molecular formula $C_4H_6N_2S$ and structural formula:

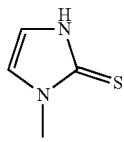

The term "methylthiouracil", as used herein, refers to 6-methyl-2-thioxo-2,3-dihydropyrimidin-4(1H)-one, CAS [56-04-2], a compound of molecular formula $C_5H_6N_2OS$ and structural formula:

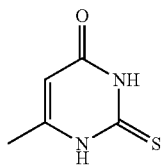

The term "Ph. Eur. 2.2.3." as used herein, refers to the "Potentiometric Determination of pH" measurement protocol [European Pharmacopoeia 8.0, 01/2008:20203, February 2014].

The term "polysaccharide", as used herein, refers to a complex carbohydrate composed of a chain of monosaccharides joined together by glycosidic bonds.

The term "polyvinylpyrrolidone", as used herein, refers to 1-ethenylpyrrolidin-2-one, CAS [9003-39-8], a compound of molecular formula $(C_6H_9NO)_n$, also known as PVP or povidone.

The terms "prevent", "preventing" and "prevention" as used herein, refer to inhibiting the inception, or decreasing the occurrence or recurrence, of a disease in a subject. Prevention may be complete (e.g. the total absence of pathological cells in a subject) or partial. Prevention also refers to a reduced susceptibility to a clinical condition.

The term "propylthiouracil", as used herein, refers to 6-propyl-2-sulfanylpyrimidin-4-one, CAS [51-52-5], a compound of molecular formula $C_7H_{10}N_2OS$ and structural formula:

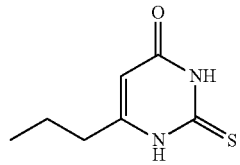

The term "subject" as used herein, refers to a mammalian, such as a human being, a non-human primate (e.g. chimpanzees, apes, monkey species), a farm animal (e.g. cattle, sheep, pigs, goats, horses), a domestic mammal (e.g. dogs, cats) or a laboratory animal (e.g. mice, rats, guinea pigs). The term does not denote any particular age or sex.

The term "therapeutically effective amount" as used herein, refers to any amount of a compound, composition or formulation which, when administered to a subject: i) prevents the inception or recurrence or ii) causes the reduction or remission of the disease or condition against which the compound, composition or formulation is effective.

The term "thioureylene" as used herein, relates to a group of compounds of general formula $R_1$—CS—$NR_2R_3$, wherein $R_1$, $R_2$ and $R_3$ are organic radicals, used in the treatment of hyperthyroiditis. Examples of thioureylene compounds include, but are not limited to, carbimazole, methimazole, methylthiouracil and propylthiouracil.

The term "treat" or "treatment" as used herein, refers to the administration of a composition or formulation of the invention to a subject in order to control the progression of a disease after its clinical signs have shown. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state, and remission (both partial and total). The control of progression of the disease also involves an extension of survival, compared with the expected survival if treatment is not applied.

2. Liquid Compositions

In a first aspect, the present invention relates to a composition comprising a thioureylene compound, a pharmaceutically acceptable salt, solvate, prodrug or combination thereof, a polysaccharide and a liquid vehicle. Preferably, the thioureylene compound is selected from the group consisting of carbimazole, methimazole, methylthiouracil, propylthiouracil, their pharmaceutically acceptable salts, solvates, prodrugs and combinations thereof. More preferably, the thioureylene compound is carbimazole, methimazole, their pharmaceutically acceptable salts, solvates, prodrugs or combinations thereof. Further preferably, the thioureylene compound is methimazole, its pharmaceutically acceptable salts, solvates, prodrugs or combinations thereof. In one embodiment, the composition comprises about 0.25% to about 1% w/v of the thioureylene compound, its pharmaceutically acceptable salts, solvates, prodrugs or combinations thereof.

In one embodiment, the polysaccharide of the composition of the invention is selected from the group consisting of amphoteric (e.g. carboxymethylchitosan, N-hydroxy-dicarboxyethyl-chitosan, modified potato starch), anionic (e.g. alginic acid, pectin, xanthan gum, hyaluronic acid, chondroitin sulfate, gum arabic, gum karaya, gum tragacanth, carboxymethyl-chitin, cellulose gum), cationic (e.g. chitosan, cationic guar gum, cationic hydroxyethylcellulose (HEC)), hydrophobic (e.g. cetyl hydroxyethylcellulose, poly-quaternium 24) and non-ionic (e.g. starch, dextrins, guar gum, cellulose ethers (such as hydroxyethylcellulose, methylcellulose or nitrocellulose)) polysaccharides and the combinations thereof. Preferably, the polysaccharide is anionic. More preferably, the anionic polysaccharide is a gum, such as xanthan gum. Examples of suitable xanthan gums that can be used in the composition of the invention include RHODIGEL® (e.g. 23, 80), KELTROL® (e.g. F, T, TF, 1000) and MEREZAN®. Preferably, a mixture of RHODIGEL® 23 and 80 is employed.

Preferably, the composition comprises at least about 0.2% w/v of the polysaccharide. More preferably, the composition comprises at least about 0.4% w/v of the polysaccharide.

The liquid vehicle according to the invention is selected from the group consisting of a hydrophobic oily carrier and water. Preferably, the hydrophobic oily carrier comprises: i) a vegetable oil, ii) one or more triglycerides of medium chain fatty acids or iii) a combination of i) and ii). Examples of vegetable oils include, but are not limited to, almond oil, cottonseed oil, olive oil, peanut oil, safflower oil, sesame oil, soybean oil, or a combination thereof. Medium chain fatty acids are $C_6$-$C_{18}$ fatty acids. Preferably, the fatty acids are saturated. More preferably, the triglyceride is selected from the group consisting of capric triglyceride, caprylic triglyceride and combinations thereof. The liquid vehicle is present in about 40% to 98% w/v, preferably in about 60 to 98% w/v, and more preferably in about 78% to about 98% w/v, of the total composition volume, depending on the nature and the amount of other excipients present in the liquid composition.

In an additional embodiment, the composition according to the invention further comprises a thickening agent. Said thickening agent includes, but is not limited to, acetylated distarch adipate, acetylated distarch phosphate, acetylated oxidized starch, acetylated starch, acid treated starch, agar, alginic acid, alkaline treated starch, aluminum distearate, ammonium alginate, arabinogalactan, bleached starch, calcium alginate, carrageenan, dextrin roasted starch, distarch phosphate, enzyme treated starch, gellan gum, guar gum, gum arabic, glycerol, hydrogenated castor oil, hydroxypropyl cellulose, hydroxypropyl distarch phosphate, hydroxypropyl methylcellulose, hydroxypropyl starch, karaya gum, konjac gum, locust bean gum, methyl ethyl cellulose, methylcellulose, monostarch phosphate, oxidized starch, pectin, phosphated distarch phosphate, potassium alginate, processed eucheuma seaweed, propane-1,2-diol alginate, polyvinylpyrrolidone, odium alginate, starch sodium octenylsuccinate, tara gum, tragacanth, triethyl citrate or a combination thereof.

In one version of this embodiment, the thickening agent is suitable for use with water. Preferably, glycerol, polyvinylpyrrolidone or a combination thereof is used as thickening agent when water is employed as liquid vehicle.

Preferred realizations of the composition of the invention when the vehicle is water include, but are not limited to, the following combinations of active agent, xanthan gum and thickening agent(s): carbimazole and xanthan gum; methimazole and xanthan gum; methylthiouracil and xanthan gum; propylthiouracil and xanthan gum; carbimazole, xanthan gum and glycerol; methimazole, xanthan gum and glycerol; methylthiouracil, xanthan gum and glycerol; propylthiouracil, xanthan gum and glycerol; carbimazole, xanthan gum and polyvinylpyrrolidone; methimazole, xanthan gum and polyvinylpyrrolidone; methylthiouracil, xanthan gum and polyvinylpyrrolidone; propylthiouracil, xanthan gum and polyvinylpyrrolidone; carbimazole, xanthan gum, glycerol and polyvinylpyrrolidone; methimazole, xanthan gum, glycerol and polyvinylpyrrolidone; methylthiouracil, xanthan gum, glycerol and polyvinylpyrrolidone; and propylthiouracil, xanthan gum, glycerol and polyvinylpyrrolidone.

In another version of the previous embodiment, the thickening agent is suitable for use with a hydrophobic oily carrier. Preferably, aluminum distearate, hydrogenated castor oil or a combination thereof is used as thickening agent in this case.

Preferred realizations of the composition of the invention when the vehicle is a mixture of capric and caprylic triglycerides include, but are not limited to, the following combinations of active agent, xanthan gum and thickening agent(s): carbimazole and xanthan gum; methimazole and xanthan gum; methylthiouracil and xanthan gum; propylthiouracil and xanthan gum; carbimazole, xanthan gum and aluminum distearate; methimazole, xanthan gum and aluminum distearate; methylthiouracil, xanthan gum and aluminum distearate; propylthiouracil, xanthan gum and aluminum distearate; carbimazole, xanthan gum and hydrogenated castor oil; methimazole, xanthan gum and hydrogenated castor oil; methylthiouracil, xanthan gum and hydrogenated castor oil; propylthiouracil, xanthan gum and hydrogenated castor oil; carbimazole, xanthan gum, aluminum distearate and hydrogenated castor oil; methimazole, xanthan gum, aluminum distearate and hydrogenated castor oil; methylthiouracil, xanthan gum, aluminum distearate and hydrogenated castor oil; and propylthiouracil, xanthan gum, aluminum distearate and hydrogenated castor oil.

Preferably, the composition comprises at least about 0.5% w/v of the thickening agent. More preferably, the composition comprises about 1.0% w/v to about 20% w/v of the thickening agent.

In a further embodiment, the composition according to the invention comprises a wetting agent. Examples of wetting agents according to the invention include, but are not limited to, beta-cyclodextrin, brominated vegetable oil, calcium stearoyl lactylate, choline salts and esters, cross-linked sodium carboxymethylcellulose, dioctyl sodium sulfosuccinate, magnesium stearate, polyglycerol polyricinoleate, polyoxyethylene stearate, polysorbate (i.e. 20, 40, 60, 65, 80), simethicone emulsion, sodium carboxymethylcellulose, sodium stearoyl lactylate, sorbitan monolaurate, sorbitan monooleate, sorbitan monopalmitate, sorbitan monostearate, sorbitan tristearate, stearyl tartarate, sucroglycerides, sucrose acetate isobutyrate, superglycerinated hydrogenated rapeseed oil, oxidized soya bean oil or a combination thereof. Preferably, simethicone emulsion is applied as wetting agent when a water-based liquid vehicle is employed. When a hydrophobic oily vehicle is used instead, polysorbate 80 is preferred as wetting agent. Preferably, the composition comprises about 0.1% to about 1.0% w/v of the wetting agent.

In an additional embodiment, the composition comprises a pH buffer solution. Preferably, the pH buffer solution is selected from the group consisting of citric acid, disodium phosphate dihydrate, sodium dihydrogen phosphate dihydrate and combinations thereof. More preferably, the pH buffer solution is utilized when a water liquid vehicle is employed. Preferably, the pH of the liquid composition is of about 3.0 to about 7.0, and more preferably of about 4.3 to 6.0, at 25° C. as measured according to Ph. Eur. 2.2.3.

In another embodiment, the composition further comprises a preservative. Examples of preservatives include, but are not limited to, benzoic acid, diphenyl (biphenyl), borax, boric acid, calcium benzoate, calcium disodium EDTA, calcium formate, calcium propionate, calcium sorbate, dehydroacetic acid, dimethyl dicarbonate, ethyl para-hydroxybenzoate, examethylene tetramine (hexamine), formaldehyde, formic acid, gum guaicum, heptyl p-hydroxybenzoate, lecithin citrate, lysozyme, methylparaben (methyl para-hydroxybenzoate), natamycin (pimaricin), nisin, orthophenyl phenol (2-hydroxybiphenyl), phytic acid, potassium benzoate, potassium propionate, potassium sorbate, propionic acid, propylparaben (propyl para-hydroxybenzoate), sodium benzoate, sodium dehydroacetate, sodium ethyl para-hydroxybenzoate, sodium formate, sodium methyl para-hydroxybenzoate, sodium orthophenyl phenol, sodium propionate, sodium propyl para-hydroxybenzoate, sodium sorbate, sodium tetraborate and thiabendazole. Preferably, the preservative is sodium benzoate. The preservative is applied, preferably, when a water-based liquid vehicle is used.

In a further embodiment, the liquid compositions of the invention comprise optionally a coloring (e.g. food yellow no. 5, food red no. 3, food blue no. 2, food lake dye, titanium dioxide, red iron oxide, yellow iron oxide) or flavoring (e.g. honey, caramel, carrot, apple, cinnamon oil) agent. The liquid compositions of the invention may also include additional ingredients commonly used in the preparation of human and veterinary products. For example, sweeteners (e.g. sugar, saccharin), antioxidants (e.g. BHT, BHA) and dispersants (e.g. calcium stearate) can be added to the compositions.

In yet another embodiment, the liquid compositions of the invention consist essentially of:
 i) about 0.25% to about 1% w/v of a thioureylene compound, a pharmaceutically acceptable salt, solvate, prodrug or combination thereof,
 ii) at least about 0.2% w/v of polysaccharide, and
 iii) a liquid vehicle.

In another embodiment, the liquid compositions of the invention consist essentially of:
 i) about 0.25% to about 1% w/v of a thioureylene compound, a pharmaceutically acceptable salt, solvate, prodrug or combination thereof,
 ii) at least about 0.2% w/v of polysaccharide
 iii) at least about 0.5% w/v of a thickening agent, and
 iv) a liquid vehicle.

3. Process of Making Liquid Compositions

In another aspect, the present invention is directed to a process of preparing the liquid composition of the invention, which comprises mixing: 1) a thioureylene compound, a pharmaceutically acceptable salt, solvate or prodrug thereof, 2) a polysaccharide and 3) a liquid vehicle. Preferably, about 0.25% to about 1% w/v of the thioureylene compound, a pharmaceutically acceptable salt, solvate, prodrug or combination thereof, at least about 0.2% w/v of the polysaccharide and the liquid vehicle are mixed according to the process of the invention. In an additional version of this aspect, the process of making the liquid composition of the invention further comprises mixing it with a thickening or wetting agent.

4. Pharmaceutical Formulations

In another aspect, the present invention relates to a pharmaceutical formulation comprising the liquid composition of the invention and at least one excipient. Preferably, the pharmaceutical formulation is suitable for oral administration such as an oral solution, oral suspension, feed premix, gels, capsule or bolus. The formulations of the invention may be produced following methods known in the art. See Gunnar A, Ed., "Remington: The Science and Practice of Pharmacy" 20th ed. (Lippincott Williams & Wilkins, Philadelphia, PA, US, 2003).

Examples of excipients which may be used for preparing the pharmaceutical formulations of the invention include, but are not limited to, solid powdery vehicles with low water content, sugar alcohols (e.g. mannitol, xylitol, sorbitol), sugars (e.g. lactose, fructose, glucose, sucrose, saccharose), cellulose and cellulose derivatives (e.g. microcrystalline cellulose, hydroxypropylcellulose, hydroxypropylmethylcellulose), mixtures and compounds, respectively, from cellulose derivatives with other excipients (e.g. silicone dioxide, guar gum, carboxymethylcellulose sodium), natural or modified starches (e.g. corn starch, potato starch), silicone dioxide and silicates (e.g. magnesium, aluminum and calcium silicate) and phosphates (e.g. calcium and magnesium phosphate), or a combination thereof.

Other suitable excipients for the stabilization of formulations include, in particular, buffers with a pH value of about 4.3 or higher, such as buffer solutions comprising citric acid, disodium phosphate dihydrate, sodium carbonate, sodium dihydrogen phosphate, sodium hydrogen carbonate, sodium hydroxide or combinations thereof.

5. Use of Liquid Compositions or Formulations for Lowering Thyroid Hormone Levels In another aspect, the present invention refers to the use of a liquid composition according to the invention and a pharmaceutical formulation containing said liquid composition for lowering thyroid hormone levels. In a particular embodiment, the liquid compositions and pharmaceutical formulations of the invention are useful for lowering the plasmatic levels of the $T_3$ and $T_4$ thyroid hormones. In a further version of this embodiment, the compositions and pharmaceutical formulations of the invention are used for treating or preventing hyperthyroidism. Preferably, the compositions and pharmaceutical formulations of the invention are used for treating hyperthyroidism.

Preferably, the liquid compositions or formulations of the invention are administered periodically, such as on a daily basis. The dosage regimen may vary according to the clinical protocols that are applicable to the subject under treatment and that are known in the art.

According to the invention, the liquid compositions can be administered by any formulation adequate for oral delivery. Suitable oral formulations include oral solutions, oral suspensions, feed premix, gels, capsules or boluses. Preferably, the liquid compositions of the invention are administered as oral pharmaceutical formulations.

This invention is further illustrated by the following examples which should not be construed as limiting. The contents of all documents cited throughout this application are incorporated herein in their entirety by reference.

General Procedures

1. Process for Making Water-Based Liquid Compositions
A. Pre-Mix

First, sodium benzoate is dissolved in 150 liters of purified water at 20-25° C. using a silverson mixer at low speed (2500 rpm). Second, polyvinylpyrrolidone K30

(FLUKA®81420, Sigma-Aldrich Company Ltd., Dorset, GB) is added to the solution and is mixed at low speed (2500 rpm). Third, xanthan gum (RHODIGEL® 80/23, Rhodia Chimie, Boulogne-Billancourt, FR) is added slowly to the blend and is mixed at low speed (2500 rpm) for 30 min or until completely dispersed. Finally, glycerol is added to the combination and is mixed at 2500 rpm for 10 min to obtain a pre-mix.

B. Active Ingredient Solution

Disodium phosphate dehydrate, sodium dihydrogen phosphate, citric acid, a thioureylene compound (e.g. carbimazole, methimazole, methylthiouracil, propylthiouracil, its pharmaceutically acceptable salt, solvate or prodrug thereof) and simethicone emulsion (DOW CORNING® Q7-2587, Dow Corning Corp., Midland, MI, US) are added one by one to 16 liters of purified water at 20-25° C. and are mixed at 2500 rpm using a silverson mixer for 10 min or until completely dissolved to obtain an active ingredient solution.

C. Liquid Composition

The pre-mix and the active ingredient solution are mixed at 2500 rpm for 15 min or until completely dispersed. Subsequently, a flavor agent is incorporated to the solution and is mixed with a silverson mixer at 2500 rpm for 5 min or until dispersed. Purified water at 20-25° C. is poured in to complete 200 liters of solution and is mixed at 2500 rpm for 10 min or until completely dispersed.

2. Process for Making Oil-Based Liquid Compositions

Polysorbate 80, aluminum distearate, hydrogenated castor oil and a thioureylene compound (e.g. carbimazole, methimazole, methylthiouracil, propylthiouracil, its pharmaceutically acceptable salt, solvate or prodrug thereof) are added one by one to 16 liters of a caprylic/capric triglyceride liquid vehicle (MIGLYOL 8100®, Dynamit Nobel GmbH, Leverkusen, DE) and are mixed at 2500 RPM using a silverson mixer for 10 min or until completely dissolved. The caprylic/capric triglyceride mixture is poured in to complete 200 liters of solution and is mixed at 2500 rpm for 10 min or until completely dispersed.

Example 1

Water-Based Liquid Compositions

Water-based liquid compositions having the ingredients and content in weight by volume percentage of Table 1 were prepared according to the protocols above.

TABLE 1

| Ingredient | O-MET-010 | O-MET-030 | O-MET-040 |
|---|---|---|---|
| Methimazole | 0.5% | 0.5% | 0.5% |
| Sodium benzoate | 0.15% | 0.15% | 0.15% |
| Glycerol | 15% | 15% | 15% |
| Polyvinylpyrrolidone K30 | 1% | 1% | 1% |
| Xanthan gum | 0.4% | 0.2% | — |
| Disodium phosphate dehydrate | 0.25% | 0.25% | 0.25% |
| Sodium dihydrogen phosphate | 1.02% | 1.02% | 1.02% |
| Citric acid | 0.325% | 0.325% | 0.325% |
| Honey flavor | 0.2% | 0.2% | 0.2% |
| Simethicone emulsion | 0.2% | 0.2% | — |
| Purified water | 81.95% | 82.15% | 82.55% |

Aliquots of the O-MET-010 solution were stored at: i) 25° C. and 60% relative humidity ("RH"), ii) 30° C. and 65% RH and iii) 40° C. and 75% RH. The stability of the aliquots was assayed after 1 year of storage. All aliquots were found to be stable.

Compositions containing 0% and 0.2% w/v (i.e. O-MET-040, O-MET-030) instead of 0.4% w/v xanthan gum (i.e. O-MET-010) were prepared according to the protocols above. The compositions were stored at 40° C. and 75% RH for 1 year. After this period, the stability of the compositions was assayed. The O-MET-030 and O-MET-040 solutions were found to be unstable.

Example 2

Oil-Based Liquid Compositions

An oil-based liquid composition having the ingredients and content in weight by volume percentage of Table 2 was prepared according to the protocols above.

TABLE 2

| Ingredient | O-MET-020 |
|---|---|
| Methimazole | 0.5% |
| Polysorbate 80 | 0.5% |
| Aluminum distearate | 0.5% |
| Hydrogenated castor oil | 0.5% |
| Caprylic/capric triglycerides | 98.0% |

Aliquots of the O-MET-020 solution were stored at: i) 25° C. and 60% RH, ii) 30° C. and 65% RH and iii) 40° C. and 75% RH. The stability of the aliquots was assayed after 1 year of storage. All aliquots were found to be stable.

Example 3

Pharmacokinetic Comparison of the O-MET-010 Solution and the Felimazole® Sing Coated Tablets A pharmacokinetic study in cats following the oral administration of the O-MET-010 solution and FELIMAZOLE® 5 mg coated tablets for cats (UK marketing authorization: Vm 10434/4061; Dechra Veterinary Products Ltd., Nortwich, GB) was conducted to determine the plasma levels of methimazole. The pharmacokinetic parameters $AUC_t$ (area under the concentration/time curve), $C_{max}$ (the maximum concentration) and $T_{max}$ (time of maximum concentration) were determined.

Eighteen cats, weighing between 4-8 kg and aged between 1-8 years, were assigned to 2 treatment groups (i.e. A, B) each consisting of 9 animals. The animals were allocated in such a way as to eliminate any weight bias. The study was conducted following a staggered, two-treatment, two-period crossover protocol.

The A and B group subjects were administered the O-MET-010 solution and the Vm 10434/4061 tablets, respectively, once (period I). Then, the administration was interrupted for 30 days (washout period), and was resumed afterwards inverting the test products: the A group subjects received the Vm 10434/4061 tablets, and the B group subjects received the O-MET-010 solution once (period II). The O-MET-010 solution and the Vm 10434/4061 tablets were administered at an equivalent dose of 5 mg methimazole per animal.

Blood samples were taken by jugular catherization or venipuncture from the jugular or cephalic veins using a syringe. Immediately after collection, the samples were transferred to heparinized containers and placed on ice, prior to centrifuging and removal of the plasma. The samples were then assayed by HPLC for methimazole concentration. Table 3 shows the mean and standard deviation values of several pharmacokinetic parameters relating to the methimazole plasma levels after the oral administration of the O-MET-010 solution and Vm 10434/4061 tablet at a dose rate of 5 mg methimazole per subject. See FIG. 1.

TABLE 3

| PK parameters | O-MET-010 solution (A) | Vm 10434/4061 tablet (B) | Ratio means (A)/(B) |
|---|---|---|---|
| Cmax (ppm) | 1.13 ± 0.27 | 1.19 ± 0.25 | 94.96% |
| Tmax (hours) | 1.14 ± 1.04 | 1.02 ± 0.62 | 111.76% |
| AUC (ppm hours) | 5.85 ± 0.95 | 6.26 ± 1.25 | 93.45% |
| AUMC (ppm hours^2) | 23.30 ± 4.29 | 27.92 ± 12.32 | 83.45% |
| MRT (hours) | 3.96 ± 0.37 | 4.38 ± 1.12 | 90.41% |
| T½ (hours) | 4.35 ± 0.64 | 4.85 ± 1.18 | 89.69% |

The results above demonstrate that the O-MET-010 solution and the Vm 10434/4061 tablet formulations are bioequivalent according to the applicable USFDA regulations. See http://www.fda.gov/drugs/developmentapprovalprocess/ucm079068.htm, June 2014.

Example 4

Stability of the Liquid Compositions

Water-based liquid compositions having the ingredients and content in weight by volume percentage of the O-MET-010 solution of Table 1 were prepared according to the protocols above. Aliquots of the compositions were stored at: i) 25° C. and 60% RH, ii) 30° C. and 65% RH and iii) 40° C. and 75% RH. The stability of the aliquots was assayed after 1 year of storage. All the O-MET-010 liquid solutions were found to be stable. See Table 4.

TABLE 4

| Time | Temp | RH | Methimazole (w/v %) | pH @ 25° C. | Stability |
|---|---|---|---|---|---|
| 0 | — | — | 0.524 | 4.45 | 100% |
| 12 months | 25° C. | 60% | 0.537 | 4.43 | 100% |
| 12 months | 30° C. | 65% | 0.537 | 4.46 | 100% |
| 12 months | 40° C. | 75% | 0.526 | 4.38 | 100% |

The invention claimed is:

1. An oral liquid composition comprising:
   i) from about 0.25% to about 1% w/v of methimazole, a pharmaceutically acceptable salt thereof, a solvate thereof, or a prodrug thereof,
   ii) a non-ionic polysaccharide,
   iii) a thickening agent, which is glycerol, polyvinylpyrrolidone or a combination thereof, and
   iv) a liquid vehicle.

2. The composition of claim 1, which comprising at least about 0.2% w/v of the non-ionic polysaccharide.

3. The composition of claim 1, wherein the non-ionic polysaccharide is a cellulose ether.

4. The composition of claim 3, wherein the cellulose ether is selected from hydroxyethyl cellulose, methylcellulose, nitrocellulose, hydroxypropyl cellulose, hydroxypropyl methyl cellulose.

5. The composition of claim 1, wherein the liquid vehicle is selected from the group consisting of a hydrophobic oily carrier and water.

6. The composition according to claim 5, wherein the hydrophobic oily carrier comprises a triglyceride of C6-C18 chain fatty acid.

7. The composition according to claim 6, wherein the triglyceride is selected from the group consisting of capric triglyceride, caprylic triglyceride and combinations thereof.

8. The composition according to claim 1, wherein the thickening agent is at least about 0.5% w/v of the total composition volume.

9. The composition according to claim 1, further comprising a wetting agent.

10. The composition according to claim 9, wherein the wetting agent is 0.1% to about 1.0% w/v of the total composition volume.

11. The composition according to claim 9, wherein the wetting agent is selected from the group consisting of polysorbate 80, simethicone emulsion and combinations thereof.

12. The composition according to claim 1, further comprising a pH buffer solution.

13. The composition according to claim 12, wherein the pH buffer solution is selected from the group consisting of citric acid, disodium phosphate dihydrate, sodium dihydrogen phosphate dihydrate and combinations thereof.

14. The composition according to claim 12, wherein the pH of the composition is at least about 4.3 or more.

15. The composition according to claim 1, further comprising a preservative.

16. The composition according to claim 1, wherein the preservative comprises sodium benzoate or potassium benzoate.

17. The composition according to claim 1, further comprising a sweetener.

18. The composition according to claim 1 further comprising a sugar.

19. The composition according to claim 18, wherein the sugar is selected from lactose, fructose, glucose, sucrose and saccharose.

* * * * *